United States Patent [19]
Fox et al.

[11] Patent Number: 6,080,547
[45] Date of Patent: Jun. 27, 2000

[54] DETECTION AND SPECIATION OF CAMPYLOBACTER

[75] Inventors: Andrew John Fox, Manchester; Dennis Mackay Jones, Stockport, both of United Kingdom

[73] Assignee: Public Health Laboratory Service Board, London, United Kingdom

[21] Appl. No.: 09/363,639

[22] Filed: Jul. 30, 1999

Related U.S. Application Data

[63] Continuation of application No. 08/604,991, filed as application No. PCT/GB94/01967, Sep. 9, 1994, Pat. No. 6,001,565.

[30] Foreign Application Priority Data

Sep. 9, 1993 [GB] United Kingdom .................. 9318751

[51] Int. Cl.[7] .............................. C12Q 1/68; C12P 19/34; C07H 19/00; C07H 21/04
[52] U.S. Cl. .................................. 435/6; 435/5; 435/91.1; 435/91.2; 536/22.1; 536/23.1; 536/24.3; 536/24.31; 536/24.33
[58] Field of Search ................................. 435/5, 6, 91.1, 435/91.2; 536/22.1, 23.1, 24.3, 24.31, 24.33

[56] References Cited

FOREIGN PATENT DOCUMENTS 0 350 391  1/1990  European Pat. Off. .

OTHER PUBLICATIONS

Alm, R.A., et al., "Distribution and Polymorohism of the Flagellin Genes from Isolates of *Campylobacter coli* and *Campylobacter jejuni*," *J. Bacteriol.* 175:3051–3057 (1993).

Birkinhead, D., et al., "PCR for the Detection and Typing of Campylobacters," *Lett. Appl. Microbiol.* 17:235–237 (1993).

Bolton, F.J., et al., "Development of a Blood–free Campylobacter Medium: Screening Tests on Basal Media and Supplements, and the Ability of Selected Supplements to Facilitate Aerotolerance," *J. Appl. Bacteriol.* 54:115–125 (1983).

Giesendorf, B.A.J. et al., "Rapid and Sensitive Detection of Campylobacter spp. In Chicken Products by Using the Polymerase Chain Reaction," *Appl. Env. Microbiol.* 58:3804–3808 (1992).

Dialog File 351, Accession No. 90–010125/02, Derwent WPI English Language abstract for EP 0 350 392 (Document AL1).

Products Catalogue, New England Biolabs, Inc., Beverly, MA, pp. 7–31 (1986).

Nachamkin et al. "Flagellin gene typing of *campylobacter jejuni* by restriction fragment length polymorphism analysis" Journal of clinical microbiology, vol. 31, pp. 1531–1536, Jun. 1993.

Wegmuller et al. "Direct polymerase chain reaction detection of *campylobacter jejuni* and *campylobacter coli* in raw milk and dairy products" Applied and enviromental microbiology vol. 59, pp. 2161–2165, Jul. 1993.

Sigma Chemicla Company, Biochemicals compounds for research and diagnostic reagents p. 1639, 1990.

*Primary Examiner*—Jezia Riley
*Attorney, Agent, or Firm*—Sterne, Kessler, Goldstein & Fox P.L.L.C.

[57] ABSTRACT

Method for detecting Campylobacter by PCR detection of DNA sequence highly conserved between species *lari, coli, jejuni* and *upsaliensis*. Speciation between these four is possible as the PCR product is differentially cleaved by restriction endonucleases.

11 Claims, 8 Drawing Sheets

FIG.2(I)

```
tgattaacaaattatcatttttaagaaaaatgtataattctataatcttctc
----+----+----+----+----+----+----+----+----+----+
actaattgttttatagtaaaattcttttacatattaattataagatattagaagag D  *  Q  N  Y  H  F  *  E  K  M  Y  N  *
 *  L  T  K  L  S  F  L  R  K  N  V  *  L  I  F  Y  N  L  L ttgttatcaaaatttaaggagaaagtcgatgcatccagtaatgtattaaattacgac
----+----+----+----+----+----+----+----+----+----+
aacaatagttttaaaattcctcctttcagctacgtaggtccattacataattaatgctg

L  L  S  K  I  L  R  R  K  S  M  H  P  G  N  V  L  N  Y  D tatacggttgcaagatatttatgtttgcgaccatattgtttggcattgttggtatggct
----+----+----+----+----+----+----+----+----+----+
atatgccaacgttctataaataacaaacgctggtataacgtaacaaccataccga

Y  T  V  A  R  Y  F  M  F  A  T  I  L  F  G  I  V  G  M  A

Alu I                    Dra I ataggaactcttatagcttttcaaatgcatatcctaatttaaattatttaccaggacaa
----+----+----+----+----+----+----+----+----+----+
tatccttgagaatatcgaaaagtttaccgtataggattaaatttaataatgtcctgtt

I  G  T  L  I  A  F  Q  M  A  Y  P  N  L  N  Y  L  P  G  Q
```

```
                Dde I
tatgccacttttttcagagacttagaccacttcatacttcaggtgtgatttttggttttatg
----+----|----+----|----+----|----+----|----+----|----+----|
atacggtgaaaaagttctgaatctggtgaagtatgaagtcccacta aaaaccaaaatac

Y  A  T  F  S  R  L  R  P  L  H  T  S  G  V  I  F  G  F  M    - ctttcaggattttgggcaacggtattataggtccgcgtgttcttaaagtgagtatggc
----+----|----+----|----+----|----+----|----+----|----+----|
gaaagtcccctaaacccgttgccatatatccaggcgcacaaga atttcactcataccg

L  S  G  I  W  A  T  V  L  Y  R  S  A  C  S  *  S  E  Y  G    - tgagtcaagatttttaatggctgttggt       1948
----+----|----+----|-------
actcagttctaaaattaccgacaacca

SIZE MARKERS ON ENDS

PENNER JEJUNI'S Alu I DIGEST

Dde I PENNER JEJUNI'S

Dra I PENNER JEJUNI'S

Alu I — Dde I
UPSALIENSIS PCR's Alu I Dde I

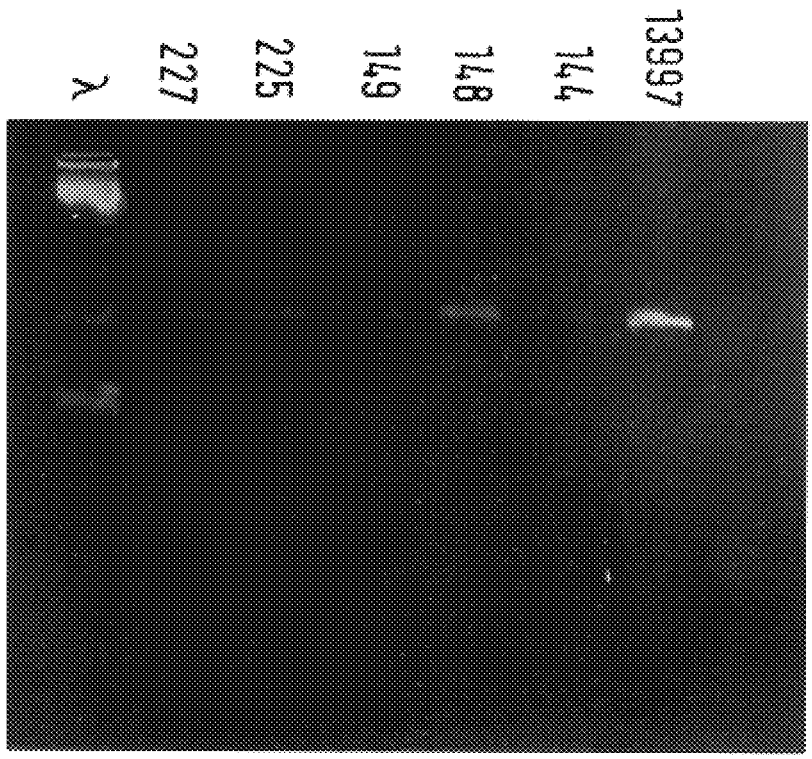
UPSALIENSIS PCR's Dra I CUT
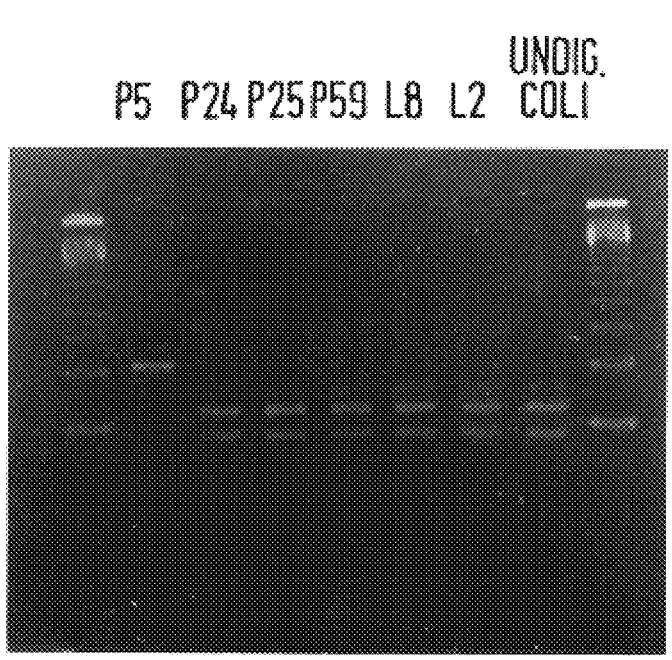
AluI - PENNER / LIOR COLI'S

C. Coli Dde I

Ora I PENNER / LIOR COLI'S

… # DETECTION AND SPECIATION OF CAMPYLOBACTER

CROSS REFERENCE TO RELATED APPLICATIONS

This application is a continuation of U.S. application Ser. No. 08/604,991, filed on Feb. 29, 1996 now U.S. Pat. No. 6,001,565, filed as PCT/GB94/01967, Sep. 9, 1994.

FIELD OF THE INVENTION

This invention relates to the detection and speciation of Campylobacter bacteria, for example in clinical, environmental and food samples. In particular, this invention relates to a method of detecting whether a sample contains Campylobacter and to a method of differentiating between the main Campylobacter species *jejune, coli, upsaliensis* and *lari*.

BACKGROUND OF THE INVENTION

Campylobacter species are recognised as the most frequent cause of bacterial gastroenteritis in the United Kingdom and many other countries throughout the world. In the U.K. approximately 90% and 10% of case isolates are identified as *Campylobacter jejuni* and *Campylobacter coli* respectively, plus a small number of other species such as *Campylobacter upsaliensis* and *lari*. The majority of the infections are sporadic the source of which remains largely unknown although the importance of several vehicles is now recognised.

There is a known desire to be able to detect and differentiate species of Campylobacter. However, it is also known that present Campylobacter enrichment culture techniques lack sensitivity, making detection difficult. *Campylobacter jejuni* does not multiply in foodstuffs and low numbers may be present together with a high background of indigenous microflora. Also, surface viable counts of Campylobacter can decrease rapidly and cells that are potentially culturable are often lost before samples reach a laboratory for analysis. Another factor making detection problematic is that antibiotics used in culture enrichment media may damage already weakened Campylobacter.

There are currently available assays for detection of a variety of food and water-borne pathogens; *L. pneumophila, V. vulnificus*, enteroinvasive *E. coli*, Shigella; but no satisfactory method of detecting Campylobacter or distinguishing between the four main Campylobacter species is known.

A method of detecting Campylobacter has been published by Giesendorf, B A J, et al in Applied and Environmental Microbiology, December 1992, pages 3804–3808. The method detects the species *jejuni, coli* and *lari*, and produces similar results to conventional methods but in a reduced time. The method suffers from a number of drawbacks. It does not enable detection of the species *upsaliensis*. Further, the method employs polymerase chain reaction (PCR) techniques but nevertheless requires a short enrichment culture before the PCR can be employed. Further still, the primer used for the PCR does not have the precise homology with DNA sequences in the three Campylobacter species that can be detected using the method.

Another method for detecting *Campylobacter jejune* and *Campylobacter coli* is known from Wegmuller, B E et al, Applied Environmental Microbiology, vol. 59, part 7, 1993 pages 2161–2165. The described method detects only the species *jejuni* and *coli*.

In addition to the above-identified problems with detection and speciation of Campylobacter, recent work on *Campylobacter jejuni* suggests that in certain circumstances it enters a "non-culturable, viable form" when subjected to environmental stresses, such as pH or temperature extremes, increased oxygen tension or nutrient depletion. In this form, Campylobacter infectivity is maintained but the organisms cannot be cultured. Thus there exists a need for the improvement of methods of detection of non-culturable forms of Campylobacter.

SUMMARY OF THE INVENTION

It is an object of this invention to provide a method of testing for the presence of Campylobacter that enables more efficient detection and eliminates or mitigates the problems with existing techniques. It is a further object to provide a method of distinguishing the Campylobacter species *jejuni, coli, upsaliensis* and *lari*.

DETAILED DESCRIPTION OF THE INVENTION

Accordingly, in a first aspect the present invention provides a method of testing for the presence of Campylobacter, e.g. in a clinical, environmental or food sample, comprising the steps of performing polymerase chain reaction (PCR) using primers adapted to amplify a region selected from (a) a sequence of at least 72 base pairs from SEQ ID NO: 1 and (b) a sequence having sufficient homology with (a) such that formation of PCR product is correlated with presence of Campylobacter; and determining if any PCR product is formed.

It is preferred that sequence (b) has at least 75% homology with (a), preferably at least 90% homology and more preferably at least 95% homology. It is also preferred that the primers are at least 12 nucleotides in length, preferably between 19–22 nucleotides in length. In particularly preferred embodiments of the invention the primers consist of at least 12 contiguous nucleotides selected from (1) SEQ ID NO:2 and SEQ ID NO:3, (2) SEQ ID NO:4 and SEQ ID NO:5 and (3) sequences having sufficient homology with (1) or (2) such that formation of PCR product is correlated with presence of Campylobacter PCR has become a well known and established tool for DNA analysis. A single gene sequence can be marketed from a large amount of other DNA and amplified to provide a suitable quantity for analysis. The basis of today's PCR was first published in 1971 be Kleppe, E et al, J. Mol. Biol., 1971, 56, 341. Further significant details and improvements on the PCR method have been added by Saiki, R K et al, Science, 1985, 230, 1350 and Mullis, K B, Sci. Am. 1990, 262, 36.

As will be appreciated by a person of skill in the art familiar with the PCR, it is important to operate at a temperature suitable to ensure that the primers used are specific for the sequence desired to be identified and amplified. To this end it is convenient to carry out the PCR reaction using the method of the invention at temperatures of at least 40° C. preferably at least 45° C. and in a particularly preferred embodiment at 48–52° C.

The 1.9 kilobase fragment identified in SEQ ID NO:1 is an underlying feature of this invention and has been found to be highly conserved between Campylobacter isolates. The method of the invention confers the advantage that PCR product will only be detected when a Campylobacter strain is found in the sample tested. The method also confers the advantage that it will detect non-culturable viable forms of Campylobacter as well as viable cells. Thus the method is effective where other methods have not been able to detect any Campylobacter.

It is preferable to use a primer sequence that will only bind to one specific region of SEQ ID NO:1 and which will not engage in formation of primer dimers and thus contaminate the PCR. Examples of preferred primers for use in the method of the invention are shown in the SEQ ID NOs 2 and 3 and SEQ ID NOs 4 and 5. These primers form further aspects of the invention.

In a second aspect the invention provides a method of distinguishing between Campylobacter species *jejuni, coli, upsaliensis* and *lari* in a DNA containing sample by performing PCR utilizing primers capable of amplifying a selected Campylobacter DNA sequence, said sequence having restriction endonuclease sites specifically associated with different Campylobacter species and then testing for digestion of the PCR product by the specific restriction endonucleases.

Thus, Campylobacter DNA that is differentially cleared by restriction endonucleases is amplified, subject to digestion by the endonucleases and identified as from a particular species.

SEQ ID NO:1 was isolated from *Campylobacter jejuni* and is known to have a particular characteristic pattern of cleavage by restriction endonucleases. *Campylobacter coli, upsaliensis* and *lari* contain sequences corresponding to SEQ ID NO:1 that have altered patterns of cleavage characteristic of each species.

In an embodiment of the second aspect there is provided a method of distinguishing between Campylobacter species *jejuni, coli, upsaliensis* and *lari*, e.g. in a clinical, environmental or food sample containing Campylobacter, comprising the steps of:
  performing polymerase chain reaction (PCR) on the sample using primers adapted to amplify a region of DNA SEQ ID NO:1 that includes nucleotides 124–196, or using primers adapted to amplify a DNA region corresponding thereto; and
  testing the PCR product for digestion by restriction endonucleases Alu I, Dra I and Dde I.

The method of the second aspect is advantageous because it enables accurate speciation between the four clinically most significant species. In particular, when amplifying region 124–196 of SEQ ID NO:1, the PCR product from *Campylobacter jejuni* is cleaved by all three restriction endonucleases, whereas the PCR product from species *coli* is not cleaved by Dra I, the PCR product from species *upsaliensis* is only cleaved by Dde I and PCR product from lari is only cleaved by Alu I. It is a straightforward matter for a person skilled in the art to identify whether the PCR product is cleaved by one or more of the above endonucleases and thus the method enables simple speciation of Campylobacter into *jejuni, coli, upsaliensis* or *lari*.

The embodiments of the first aspect of the invention described above form embodiments of the second aspect of the invention also, provided that primers are selected so as to be adapted to amplify at least nucleotides 124–196 of SEQ ID NO:1, or a Campylobacter sequence corresponding thereto.

In a preferred embodiment of the second aspect the primers consist of at least 12 contiguous nucleotides from SEQ ID NOs: 4 and 5. Where the primers are SEQ ID NOs: 4 and 5 the PCR product is 256 bp and the respective products of cleavage by Alu I, Dra I and Dde I differentiate between *jejuni, coli, upsaliensis* and *lari*.

In a further embodiment of the invention, increased sensitivity and specificity for the detection of the presence of Campylobacter DNA, e.g. in food and liquid samples, is provided by the following additional methodologies:

1. A nested PCR has been developed, and is performed by an additional round of amplification using primer sequences international primer SEQ ID NOs:4 and 5. Two exemplary primer sequences are identified as Cru 0476 (SEQ ID NO:6) and Cru 0474 (SEQ ID NO:7). Following the second round of amplification, an amplicon of approximately 173 pb is obtained in the presence of Campylobacter DNA. This DNA fragment retains the sequences for the restriction endonucleases Alu 1, Dde 1, and Dra 1, thus still enabling the speciation of the contaminating Campylobacter.

2. Additional increased sensitivity and specificity is optionally achieved by southern transfer of the amplified PCR products obtained using oligonucleotide primers SEQ ID NOs:4 and 5, followed by hybridisation with an internal probe (e.g. SEQ ID NO:8 probe sequence). The probe sequence spans the restriction sites for speciation of the contaminating Campylobacter and therefore restriction digest analysis can be used in conjunction with the probe hybridisation to confer additional specificity. The probe can be labelled, for example with digoxigenin, or radiolabelled.

The extraction procedures for food and environmental samples preferably use an internal standard to enable qualitative estimation of extraction efficiency and the effects of non-specific inhibition. The PCR "MIMIC" (Clontech Laboratories, Palo Alto, Calif.) is a form of competitive PCR in which a non-homologous neutral DNA fragment is engineered containing the same primer templates as the target DNA. The amplimer produced from this construct is a fragment either smaller or larger than the target product. Known amounts of construct are added to the PCR reaction, and compete for the same primers, acting as an internal standard. Where a mimic is used, the mimic sequence is capable of being amplified by the same primers that amplify, under PCR conditions, the Campylobacter sequence. The mimic, if cleaved by restriction endonucleases, does not form fragments that interfere with detection and/or speciation of Campylobacter—the mimic is said to be "neutral".

It is preferred to carry out the PCR steps of the invention also using a mimic. In an example, mimic DNA is added to the sample and PCR is performed according to the invention. The PCR product is analyzed. If mimic DNA has been amplified, this indicates that the PCR reaction has occurred properly. The product can then be tested for products that indicate presence of Campylobacter. If no mimic DNA is amplified then this indicates PCR has not fully been carried out, or has been inhibited in some way.

It is further preferred to carry out PCR using mimic DNA of known and varying quantities. After amplification, the various results are compared and it is observed which of the results has comparable amounts of amplified mimic and (if present) Campylobacter DNA. Thus, an estimate of the quantity of Campylobacter DNA in the original sample is obtained.

EXAMPLES

The methods of the invention are further illustrated by the further embodiments of the invention described in the following Examples:

Example 1

The PCR assay was developed by the following steps:
1> Identification of a highly conserved, species specific clone from a random library of *Campylobacter jejuni* insert fragments, cloned in the vector pBlueScript KS.
2> Chain termination sequencing of the 1.9 kilobase fragment in both directions.

3> Selection of presumptive primer pairs based on regions of equivalent G+C/A+T content, and low identity (prevention of 'primer-dimer').

4> Optimisation of reaction parameters: $Mg^{++}$ concentration, Taq enzyme source, buffer composition, annealing temperature, cycling parameters.

Example 2

Assessment of Assay Sensitivity and Specificity

Using a single amplification (35 cycles, annealing temperature 50° C.) we detected approx. 10 CFU/ml of *Campylobacter jejuni*.

At this stringency, the assay was specific for *Campylobacter jejuni*, *Campylobacter coli* and *Campylobacter upsaliensis*. Using a lower annealing temperature (42° C.), *Campylobacter fetus* and *Campylobacter lari* were also amplified.

Example 3

The following procedures were used for PCR amplification of *Campylobacter jejuni* from milk and water samples.

1> cell lysis by boiling or freeze/thaw cycles, centrifuge, PCR supernatant directly.

2> Cell lysis by boiling, nucleic acid purification by phenol/chloroform extraction.

3> cell lysis by guanidine isothiocyanate, nucleic acid purification using nuclease binding matrix ("isoquick").

4> Cell concentration using magnetic particles coated with anti-Campylobacter IgG, cell lysis by boiling.

5> concentration and immobilisation of cells on 0.2 μm nitrocellulose filters ('solid-phase' PCR).

6> Cell concentration using affinity column purification.

7> Guanidium isothiocyanate nucleic acid extraction.

with purification using silica bead matrix ('boom method')

EXTRACTION OF MILK SAMPLES FOR PCR ANALYSIS

WARM MILK TO 37° C.
↓
CENTRIFUGE @ 3,000xg, 15 MINUTES
↓
CHILL ON ICE. SEPARATE MILK AND CREAM

CREAM                                         MILK
EMULSIFY IN 10 VOLUMES
OF WARM PBS
↓                                               ↓
CENTRIFUGE @ 9,000xg, 15 MINUTES
↓

-continued

DISCARD SUPERNATANT        DISCARD SUPERNATANT

RESUSPEND MILK AND CREAM PELLETS IN
5 VOLUMES OF PBS. POOL EXTRACTS.
↓
BOIL FOR 10 MINUTES
↓
CENTRIFUGE @ 14,000xg, 5 MINUTES
↓
EXTRACT DNA WITH SILICA-BASED PURIFICATION MATRIX
↓
ELUTE NUCLEIC ACIDS WITH 2 x 50ul PURE WATER
↓
PCR NEAT SAMPLE, AND 10-FOLD SERIAL DILUTIONS

EXTRACTION OF WATER SAMPLES

PRE-FILTRATION THROUGH 30um WHATMAN FILTER
↓
CENTRIFUGE @ 9,000xg, 15 MINUTES
↓
WASH PELLET x2, 1ML PBS
↓
RESUSPEND IN 1ML STERILE WATER
↓
BOIL, 10 MINUTES
↓
EXTRACT DNA WITH SILICA-BASED
PURIFICATION MATRIX

Example 4

We observed the following differentiation of Campylobacter species using PCR primers SEQ ID NO:4 and SEQ ID NO:5 and restriction endonucleases Alu I, Dra I and Dde I.

|  | PCR product digested with: | | |
| --- | --- | --- | --- |
| Species | Alu I | Dra I | Dde I |
| C. jejuni | + | + | + |
| C. coli | + | − | + |
| C. upsaliensis | − | − | + |
| C. lari | + | − | − |

We further observed the following fragment sizes for different species.

| | Restriction enzyme digests of PCR amplimers | | | | | |
|---|---|---|---|---|---|---|
| Species | Alu I | | Dde I | | Dra I | |
| Thermophilic/ enteropathogenic | Fragment sizes (bp) | | Fragment sizes (bp) | | Fragment sizes (bp) | |
| C. jejuni | 2 | 108, 148 | 2 | 83, 173 | 2 | 123, 133 |
| C. jejuni (hippurate + ve) | 2 | 108, 148 | 2 | 83, 173 | 2 | 123, 133 |
| C. coli | 2 | 108, 148 | 2 | 83, 173 | 1 | 256 |
| C. lari | 2 | 108, 148 | 1 | 256 | 1 | 256 |
| C. upsaliensis | 1 | 256 | 3 | 30, 83, 143 | 1 | 256 |

The results are also illustrated in FIG. 3; where when bands were not visible by eye they were detected by use of radiolabels.

Example 5

To test the specificity of Campylobacter detection we used PCR primers on laboratory samples containing a wide range of organisms. The primers were SEQ ID NOs: 4 and 5, PCR product size in brackets:

| | Annealing temperature of primers | | |
|---|---|---|---|
| Species | 37° C. | 42° C. | 50° C. |
| C. jejuni | + (256) | + | + |
| C. coli | + | + | + |
| C. upsaliensis | + | + | + |
| C. fetus | + | ± | + |
| C. lari | + | ± | + |
| C. mucosalis | ± | – | – |
| C. sputorum | ± | – | – |
| Achromobacter sp. | – | – | – |
| Acinetobacter calcoac. | ± (multiple) | – | – |
| Acinetobacter sp. | ± (multiple) | – | – |
| Aeromonas hydrophila | – | – | – |
| Citrobacter freundii | – | – | – |
| Enterobact. aerogenes | – | – | – |
| Enterobact. agglomerans | ± (500) | – | – |
| Enterobacter cloacae | – | – | – |
| Escherichia coli | – | – | – |
| Flavobacterium | – | – | – |
| Klebsiella aerogenes | – | – | – |
| Klebsiella oxytoca | ± (500) | – | – |
| Proteus mirabilis | – | – | – |
| Proteus morganii | – | – | – |
| Providencia stuartii | – | – | – |
| Pseudomonas aeroginosa | – | – | – |
| Pseudomonas maltophilia | – | – | – |
| Pseudomonas pickettii | – | – | – |
| Salmonella enteritidis | – | – | – |
| Salmonella typhimurium | – | – | – |
| Serratia marcescens | – | – | – |
| Serratia liquefaciens | – | – | – |
| Shigella dysenteriae | – | – | – |
| Shigella sonnei | – | – | – |
| Vibrio cholera | – | – | – |
| Vibrio furnassii | ± (1000) | – | – |
| Vibrio parahaemolyticus | ± (180) | ± | – |
| Yersinia enterocolitica | – | – | – |
| Oxford Staphlococcus | ± (300) | ± | – |

Example 6

Using standard culture techniques (published by Bolton F J, et al, J. Appl. Bacteriol., 1983, vol. 54, pages 115–125) we compared the detection of *Campylobacter jejuni* by culture with detection by the method of the invention (using primers SEQ ID NOs: 4 and 5) against time.

The success of culture detection declined over the time of the comparison, no culturable organisms being found remaining in the sample after 26 days—thus at this point detection by culture indicated no Campylobacter present.

By contrast, using the PCR method of the of the invention we were still able to detect Campylobacter DNA in a sample 42 days old. The results are illustrated in FIG. 1.

Example 7

To confirm the accuracy of the PCR method of the invention we tested many samples that contained known species of Campylobacter. The results, illustrated in FIGS. 4–11, confirm the method is completely accurate for all samples tested, and correctly identified each one by species.

FEATURES OF THE PCR ASSAY FOR *Campylobacter jejuni*

It allows rapid and sensitive detection of *Campylobacter jejuni* from environmental samples, provides a semi-quantitative indication of the bacterial load, and determines whether samples are contaminated with *Campylobacter jejuni, coli, upsaliensis* or *lari*.

The method is of use for examining epidemiology of Campylobacter infection such as a) seasonal peak, b) inverse correlation of surface water viable counts with human disease, c) role of water supply in (re)infection of broiler flocks with *Campylobacter jejuni*, d) contamination of foodstuffs at the point of sale, and e) determine origin of sporadic human infections.

Thus, a novel method incorporating polymerase chain reaction assay has been developed for the detection of Campylobacter in clinical, environmental and food samples, such as milk and water samples. The assay is rapid, highly sensitive, and specific for Campylobacter sp. Simple restriction analysis of the PCR product allows speciation between *Campylobacter jejuni, coli, upsaliensis* and *lari*.

DESCRIPTION OF DRAWINGS

FIG. 2 shows the sequence (SEQ ID NOs: 12, 14–19) of open reading frame "C" from insert fragment pBSKSCJ19B with primer/nested primer locations, and restriction sites.

FIGS. 4–11 shows the results of carrying out the PCR method of the invention on samples containing a wide ranges of known isolates. "P"=Penner Serotype Reference strains. "L"=Lior Serotype Reference Strains. Others are laboratory isolates. Standard size markers are on the gel ends.

Figure 1:
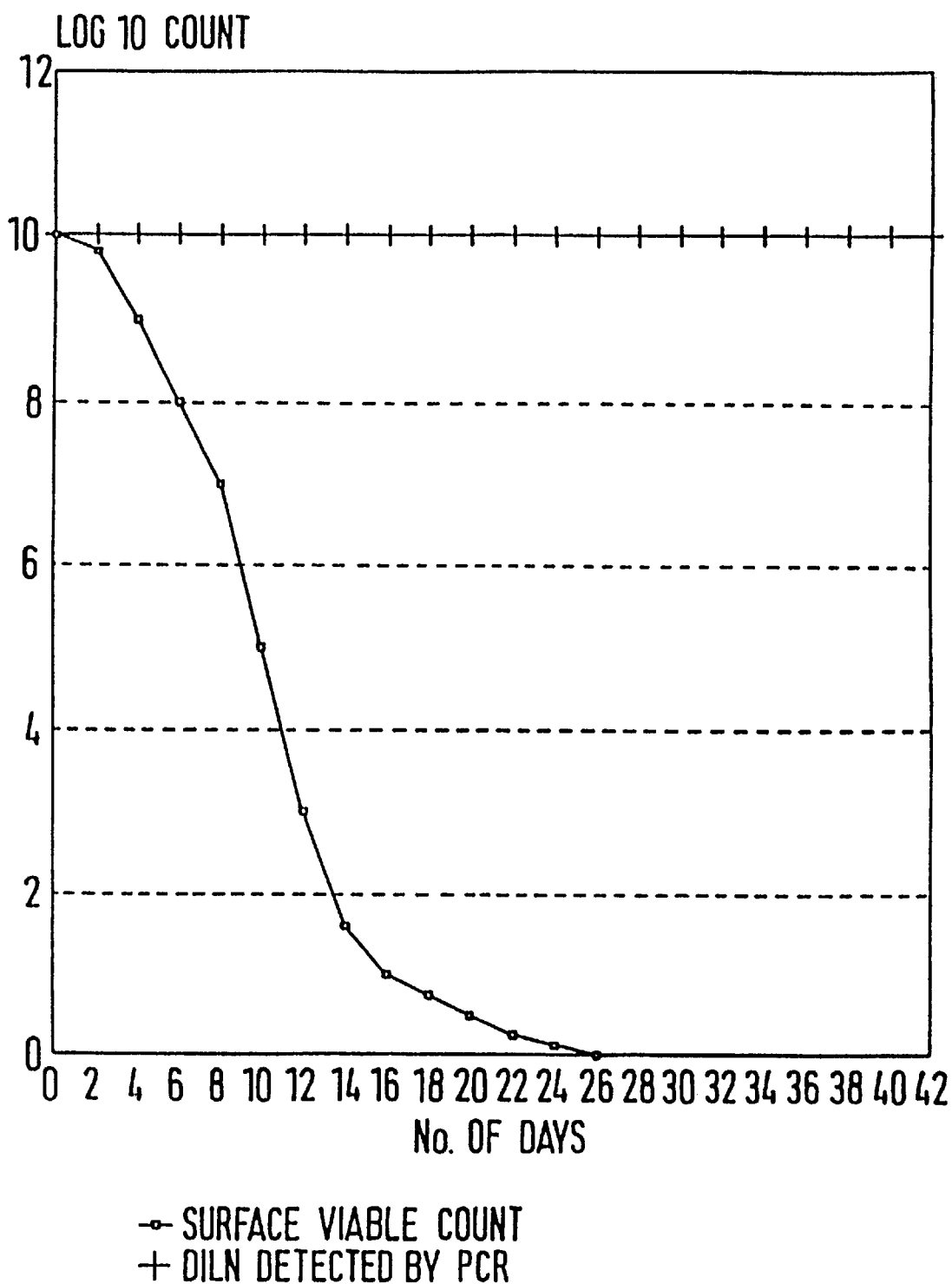
FIG. 1 shows a comparison of culturability of *Campylobacter jejuni* against time with detection of *Campylobacter jejuni* using PCR of the invention.
Figure 3:
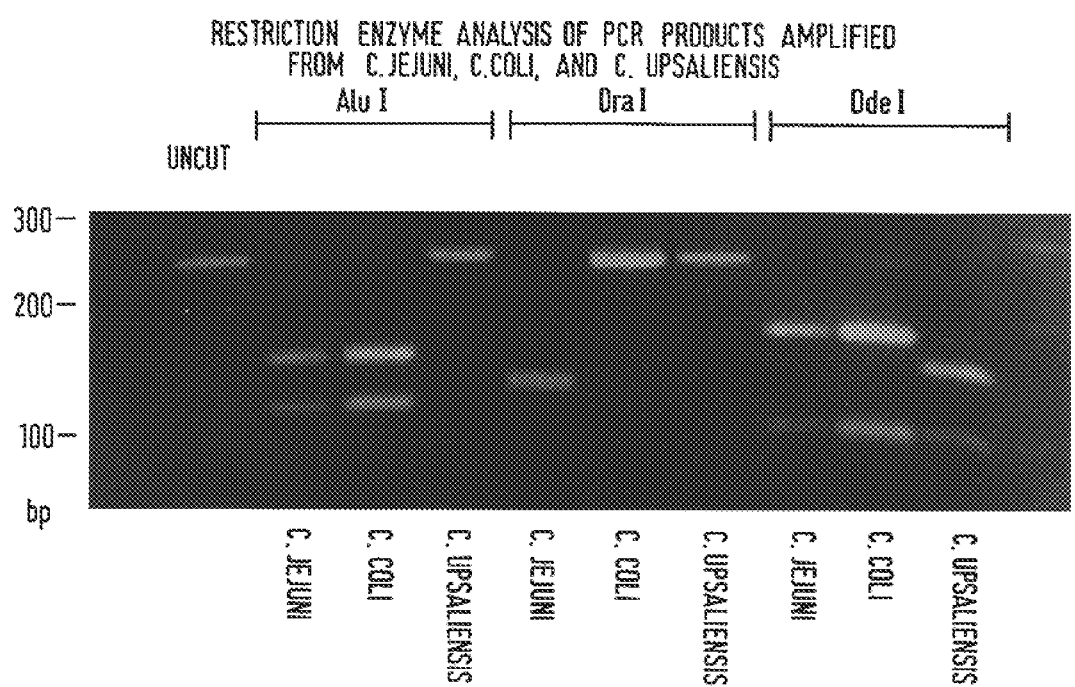
FIG. 3 shows restriction enzyme analysis of PCR products amplified from *C. jejuni, coli* and *upsaliensis*.
Figure 4:
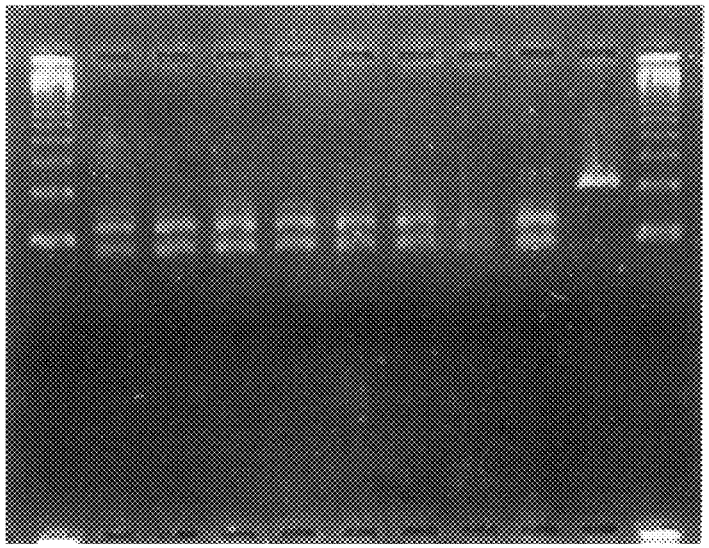
Figure 5:
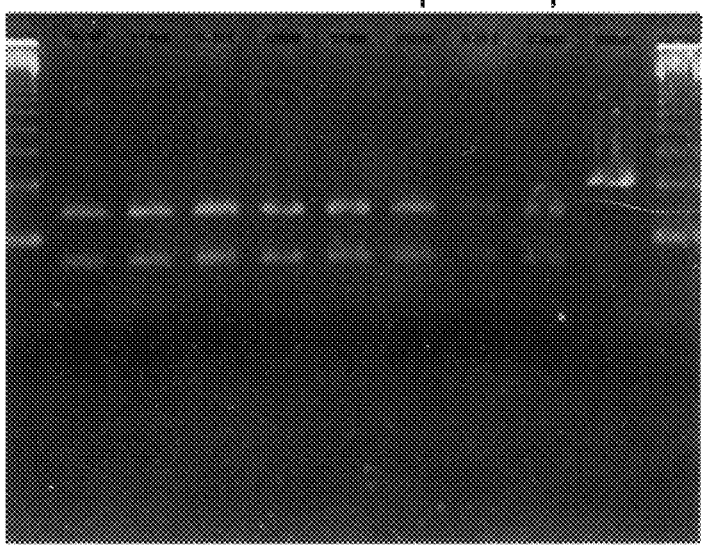
Figure 6:
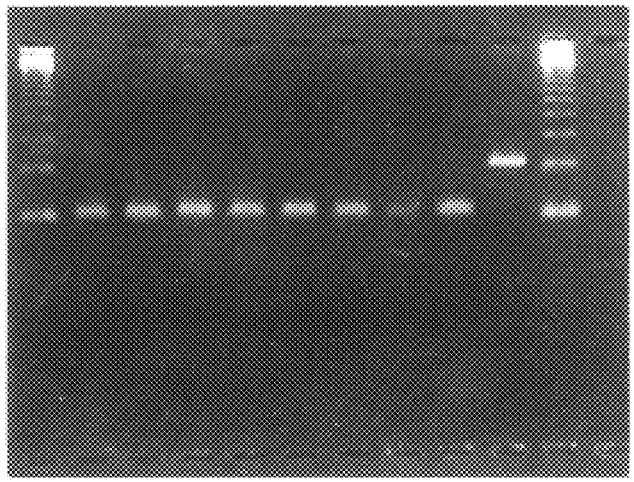
Figure 7:
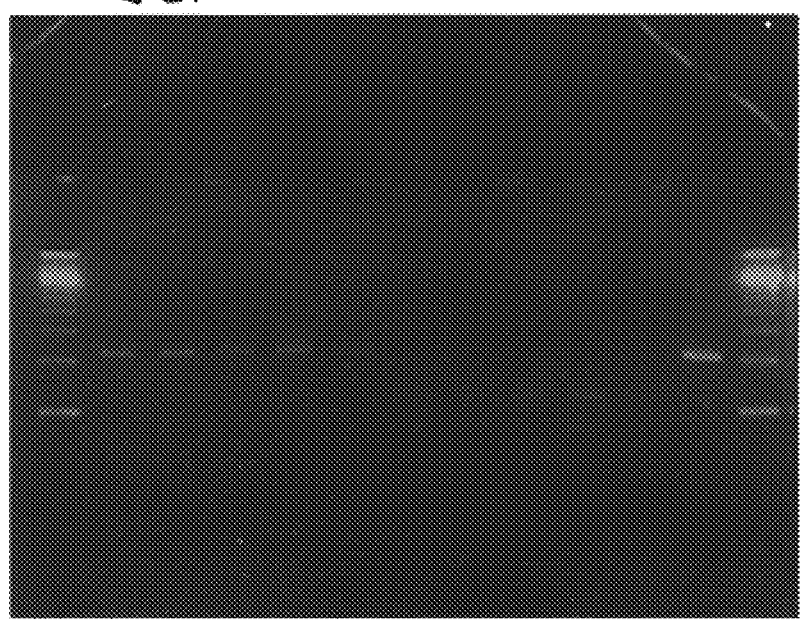
Figure 10:
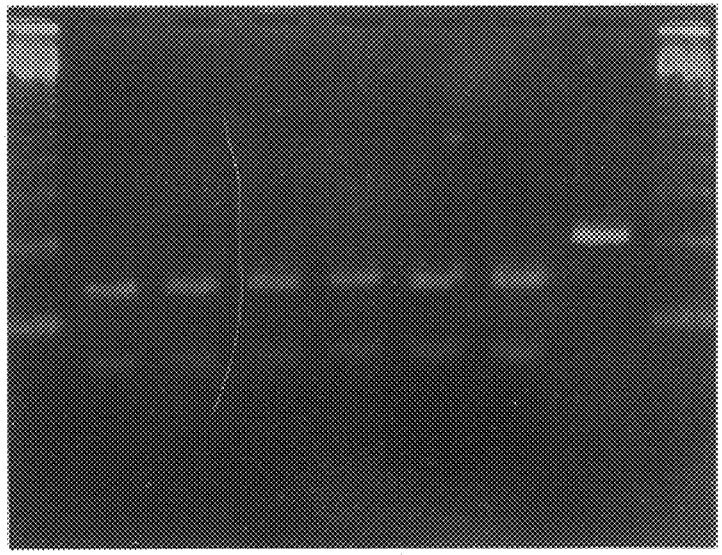
Figure 11:

| | | |
|---|---|---|
| FIG. 4 | *C. Jejuni.* | Alu I digest. |
| FIG. 5 | *C. Jejuni.* | Dde I digest. |
| FIG. 6 | *C. Jejuni.* | Dra I digest. |
| FIG. 7 | *C. upsaliensis.* | Alu I and Dde I digest. |
| FIG. 8 | *C. upsaliensis.* | Dra I digest. |
| FIG. 9 | *C. Coli.* | Alu I digest |
| FIG. 10 | *C. Coli.* | Dde I digest |
| FIG. 11. | *C. Coli.* | Dra I digest |

```
Sequence ID No. 1
  1 accaacagcc attaaaaatc ttgactcagc catactcact ttaagaacac
    tggttgtcgg taatttttag aactgagtcg gtatgagtga aattcttgtg 51 gcggacctat ataataccgt tgcccaaatc cctgaaagca taaaaccaaa
    cgcctggata tattatggca acgggtttag ggactttcgt attttggttt 101 aatcacacct gaagtatgaa gtggtctaag tcttgaaaaa gtggcatatt
    ttagtgtgga cttcatactt caccagattc agaactttt caccgtataa 151 gtcctggtaa ataatttaaa ttaggatatg ccatttgaaa agctataaga
    caggaccatt tattaaattt aatcctatac ggtaaacttt tcgatattct 201 gttcctatag ccataccaac aatgccaaac aatatggtcg caaacataaa
    caaggatatc ggtatggttg ttacggtttg ttataccagc gtttgtattt 251 atatcttgca accgtatagt cgtaatttaa tacattacct ggatgcatcg
    tatagaacgt tgcatatca gcattaaatt atgtaatgga cctacgtagc 301 actttctcct taaaattttt gataacaaga gaagattata gaatattaat
    tgaaagagga attttaaaaa ctattgttct cttctaatat cttataatta 351 tatacatttt ttcttaaaaa tgat/aatttt gttaatcatt tgttatgttt
    atatgtaaaa aagaattttt acta ttaaaa caattagtaa acaatacaaa 401 tatatttaa ggctaaatca gtcttattta ttgatattta tcttataacc
    atataaaatt ccgatttagt cagaataaat aattataaat agaatattgg 451 taaacttgtc acattttta taaaatcttc acccacttta tctcttactc
    atttgaacag tgtaaaaaat attttagaag tgggtgaaat agagaatgag 501 ttttttataaa agttcta{aca gcagtatcgc tcacatgt}c acctatccaa
    aaaaatattt tcaagat tgt cgtcatagcg agtgtaca g tggataggtt 551 acattttct taatatcttc atgcaaaacc aaagctccag gttgctttaa
    tgtaaaaaga attatagaag tacgttttgg tttcgaggtc caacgaaatt 601 aagcaaagaa ataaagcca attctttttt agttaaaaca atttctccac
    ttcgtttctt tattttcggt taagaaaaaa tcaattttgt taaagaggtg 651 cactgtaaat taaagttcgt ttattttgt taaattgata ttcttcagaa
    gtgacattta atttcaagca aataaaaaca atttaactat aagaagtctt 701 attttacaa gcatatttgc ttcaatttt tcacctatca gataatctaa
    taaaaatgtt cgtataaacg aagttaaaaa agtggatagt ctattagatt 751 aactttaaac aactcttcta tatcaacagg tttaatcaaa tatttatcta
    ttgaaatttg ttgagaagat atagttgtcc aaattagttt ataaatagat 801 taccaatatc aatagaacgc aaaagtctct ctt tctctga atacgcacta
    atggttatag ttatcttgcg ttttcagaga gaa{agagact tatgcgtgat 851 aga acaacaa ttgggacatc atctgaaatt tctttaatct ctcttgccat
    tct tgttgaa aaccctgtag tagactttaa agaaattaga gagaacggta 901 atccagtcca tccataatag gcatagcaat atctgtgata actaaatctg
    taggtcaggt aggtattatc cgtatcgtta tagacactat tgatttagac 951 gcttaaattt tttaaatttt ttaagcccct catctccatt ttgagctccg
    cgaatttaaa aaatttaaaa aattcggggt gtagaggtaa aactcgaggc
```

```
1001 attactttac taaagcgttc gcttaatata ttaatcattg attctctagc
     taatgaaatg atttcgcaag cgaattatat aattagtaac taagagatcg 1051 cttaacctca tcttcaacta ctaatattat taattcttta cattcttgtg
     gaattggagt agaagttgat gattataata attaagaaat gtaagaacac 1101 acat/ttctac tctaccctct cttttagttt taaaaatatc tcaaaacaag
     tgta aagatg agatgggaga gaaaatcaaa atttttatag agttttgttc 1151 ccccgtcttt tccattttta acttttattt ttccttggaa acttttcgata
     ggggcagaaa aggtaaaaat tgaaaataaa aaggaacctt tgaaagctat 1201 atttgtctac ttatataaag tcctactcct ataccttgac taggatgttt
     taaacagatg aatatatttc aggatgagga tatggaactg atcctacaaa 1251 tgttgtaaaa taaggttgaa aaattttatc taaattttct ttatcaatcc
     acaacatttt attccaactt tttaaaatag atttaaaaga aatagttagg 1301 caccagcatt atcttttatt gtaattttca gataatttt tccaaatttt
     gtggtcgtaa tagaaaataa cattaaaagt ctattaaaaa aggtttaaaa 1351 gaaaaattta ttgttatgat tttccttttt ttgttttaa atgcttctat
     cttttaaat aacaatacta aaaggaaaaa aacaaaaatt tacgaagata 1401 tgaatttaaa atcaaattaa gaaaactct tattaaacca ttctcatatg
     acttaaattt tagtttaatt cttttgaga ataatttggt aagagtatac 1451 ccaaaacttc ataatcactt ttcgaaacaa tattaatatt tacatgattt
     ggttttgaag tattagtgaa aagctttgtt ataattataa atgtactaaa 1501 ttttctatag tttcaaaagc aattccaag gctttattta agtctcttt
     aaaagatatc aaagtttcg ttaaggttc cgaaataaat ttcagagaaa 1551 tataaataca cactgctcta ctcctttgtt aaacaaagtt ctaaacacat 1601 caattgtttc tgacatattt ttaatcatat cttttgattg tgagtaaatt
     gttaacaaag actgtataaa aattagtata gaaaactaac actcatttaa 1651 tcagcaaatc cttttcatc tttaagattt tgcttcattt gaaacatggc
     agacgtttag gaaaagtag aaattctaaa acgaagtaaa ctttgtaccg 1701 aataccgagc tcatttaacg gttgtctcca ttgatgtgct atatcactaa
     ttatggctcg agtaaattgc caacagaggt aactcacga tatagtgatt 1751 tcatttgttc taatgaagat ttcaaaatct cttcatatgc tattttaata
     agtaaacaag attacttcta aagtttaga gaagtatacg ataaaattat 1801 tcttttcat ttttttccaa ggcaatttgc attttttct caaatttttt
     agaaaaagta aaaaaggtt ccgttaaacg taaaaaaga gtttaaaaaa 1851 acctaactgt ataaattctt gttggtgatt tttaactgta ttttcaagat
     tggattgaca tatttaagaa caaccactaa aaattgacat aaaagaacta 1901 taatacttaa ttctcttaat ttagcgtgat ttagagcaag ctcttcat
     attatgaatt aagagaatta aatcgcacta aatctcgttc gagaagta
```

SEQ ID NO: 8
Probe sequence
(173 bp amplimer from nested primers)

```
tacgactatacggttgca agatattttatgtttgcg
-----+---------+---------+---------+
atgctgatatgccaacgttctataaaatacaaacgc

Y  D  Y  T  V  A  R  Y  F  M  F  A accatattgtttggcattgttggtatggct
    ---------+---------+---------+1740
    tggtataacaaaccgtaacaaccataccga
    T  I  L  F  G  I  V  G  M  A  -

Alu I
    ataggaactcttatagcttttcaaatggca
1741 ---------+---------+---------+
    tatccttgagaatatcgaaaagtttaccgt
    I  G  T  L  I  A  F  Q  M  A  -
```

```
              Dra I
       tatcctaatttaaattatttaccaggacaa
       ---------+---------+---------+1800
       ataggattaaatttaataaatggtcctgtt
        Y  P  N  L  N  Y  L  P  G  Q   -

Dde I
       tatgccacttttt caagacttagaccacttcatacttcaggtgtgat
1801   ---------+---------+---------+---------+-------
       atacggtgaaaaagttctgaatctggtgaagtatgaagtccacacta
        Y  A  T  F  S  R  L  R  P  L  H  T  S  G  V  I
```

PCR MIMIC primers and sequence
Primer 1 Cru 0477   (SEQ ID NO: 9)
5'      agaacacgcggacctatatacgcaagtgaaatctcctccg 3'  40 mer Primer 2 Cru 0660   (SEQ ID NO: 10)
5'      cgatgcatccaggtaatgtattctgtcaatgcagtttgtag 3'  41 mer MIMIC SEQUENCE     (SEQ ID NO: 11)
    agaacacgcg gacctatata cgcaagtgaa atctcctccg tcttggagaa gggagagcgt ttgccccagc taccattgat gtgtacatga tcatggtcaa atgctggatg attgatgcag acagccgtcc caagtttcgt gagctgattg cagagttctc caaaatggct cgtgaccctc cccgctatct tgttatacag ggagatgaaa ggatgcactt gcctagccct acagattcca agttttatcg caccctgatg gaggaggagg acatggaaga cattgtggat gcagatgagt atcttgtccc acaccagggc ttttttcaaca tgccctctac atctcggact cctcttctga gttcattgag cgctactagc aacaattctg ctacaaactg cattgacaga          3'

---

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 1947 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Campylobacter coli (xi) SEQUENCE DESCRIPTION: SEQ ID NO: 1:

ACCAACAGCC ATTAAAAATC TTGACTCAGC CATACTCACT TTAAGAACAC GCGGACCTAT     60

ATAATACCGT TGCCCAAATC CCTGAAAGCA TAAAACCAAA AATCACACCT GAAGTATGAA    120

GTGGTCTAAG TCTTGAAAAA GTGGCATATT GTCCTGGTAA ATAATTTAAA TTAGGATATG    180

CCATTTGAAA AGCTATAAGA GTTCCTATAG CCATACCAAC AATGCCAAAC AATATGGTCG    240

CAAACATAAA ATATCTTGCA ACCGTATAGT CGTAATTTAA TACATTACCT GGATGCATCG    300

ACTTTCTCCT TAAAATTTTT GATAACAAGA GAAGATTATA GAATATTAAT TATACATTTT    360

TTCTTAAAAA TGATAATTTT GTTAATCATT TGTTATGTTT TATATTTTAA GGCTAAATCA    420

```
GTCTTATTTA TTGATATTTA TCTTATAACC TAAACTTGTC ACATTTTTA TAAAATCTTC      480

ACCCACTTTA TCTCTTACTC TTTTTATAAA AGTTCTAACA GCAGTATCGC TCACATGTCA      540

CCTATCCAAA CATTTTTCTT AATATCTTCA TGCAAAACCA AAGCTCCAGG TTGCTTTAAA      600

AGCAAAGAAA TAAAAGCCAA TTCTTTTTTA GTTAAAACAA TTTCTCCACC ACTGTAAATT      660

AAAGTTCGTT TATTTTTGTT AAATTGATAT TCTTCAGAAA TTTTTACAAG CATATTTGCT      720

TCAATTTTTT CACCTATCAG ATAATCTAAA ACTTTAAACA ACTCTTCTAT ATCAACAGGT      780

TTAATCAAAT ATTTATCTAT ACCAATATCA ATAGAACGCA AAAGTCTCTC TTTCTCTGAA      840

TACGCACTAA GAACAACAAT TGGGACATCA TCTGAAATTT CTTTAATCTC TCTTGCCATA      900

TCCAGTCCAT CCATAATAGG CATAGCAATA TCTGTGATAA CTAAATCTGG CTTAAATTTT      960

TTAAATTTTT TAAGCCCCTC ATCTCCATTT TGAGCTCCGA TTACTTTACT AAAGCGTTCG     1020

CTTAATATAT TAATCATTGA TTCTCTAGCC TTAACCTCAT CTTCAACTAC TAATATTATT     1080

AATTCTTTAC ATTCTTGTGA CATTTCTACT CTACCCTCTC TTTTAGTTTT AAAAATATCT     1140

CAAAACAAGC CCCGTCTTTT CCATTTTTAA CTTTTATTTT TCCTTGGAAA CTTTCGATAA     1200

TTTGTCTACT TATATAAAGT CCTACTCCTA TACCTTGACT AGGATGTTTT GTTGTAAAAT     1260

AAGGTTGAAA AATTTTATCT AAATTTTCTT TATCAATCCC ACCAGCATTA TCTTTTATTG     1320

TAATTTTCAG ATAATTTTTT CCAAATTTTG AAAAATTTAT TGTTATGATT TTCCTTTTTT     1380

TGTTTTTAAA TGCTTCTATT GAATTTAAAA TCAAATTAAG AAAAACTCTT ATTAAACCAT     1440

TCTCATATGC CAAAACTTCA TAATCACTTT TCGAAACAAT ATTAATATTT ACATGATTTT     1500

TTTCTATAGT TTCAAAAGCA ATTTCCAAGG CTTTATTTAA AGTCTCTTTT ATAAATACAC     1560

ACTGCTCTAC TCCTTTGTTA AACAAAGTTC TAAACACATC AATTGTTTCT GACATATTTT     1620

TAATCATATC TTTTGATTGT GAGTAAATTT CAGCAAATCC TTTTTCATCT TTAAGATTTT     1680

GCTTCATTTG AAACATGGCA ATACCGAGCT CATTTAACGG TTGTCTCCAT TGATGTGCTA     1740

TATCACTAAT CATTTGTTCT AATGAAGATT TCAAAATCTC TTCATATGCT ATTTTAATAT     1800

CTTTTTCATT TTTTTCCAAG GCAATTTGCA TTTTTTTCTC AAATTTTTTA CCTAACTGTA     1860

TAAATTCTTG TTGGTGATTT TTAACTGTAT TTTCAAGATT AATACTTAAT TCTCTTAATT     1920

TAGCGTGATT TAGAGCAAGC TCTTCAT                                          1947

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

TCTTAGTGCG TATTCAGAGA                                                    20

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)
```

```
       (xi) SEQUENCE DESCRIPTION: SEQ ID NO: 3:

ACAGCAGTAT CGCTCACATG T                                              21

(2) INFORMATION FOR SEQ ID NO: 4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 4:

AGAACACGCG GACCTATATA                                                20

(2) INFORMATION FOR SEQ ID NO: 5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 5:

CGATGCATCC AGGTAATGTA T                                              21

(2) INFORMATION FOR SEQ ID NO: 6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 6:

ATCACACCTG AAGTATGA                                                  18

(2) INFORMATION FOR SEQ ID NO: 7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 7:

TACGACTATA CGGTTGCA                                                  18

(2) INFORMATION FOR SEQ ID NO: 8:

(i) SEQUENCE CHARACTERISTICS:
            (A) LENGTH: 173 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 8:

TACGACTATA CGGTTGCAAG ATATTTTATG TTTGCGACCA TATTGTTTGG CATTGTTGGT    60
```

```
ATGGCTATAG GAACTCTTAT AGCTTTTCAA ATGGCATATC CTAATTTAAA TTATTTACCA        120

GGACAATATG CCACTTTTTC AAGACTTAGA CCACTTCATA CTTCAGGTGT GAT               173
```

(2) INFORMATION FOR SEQ ID NO: 9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
AGAACACGCG GACCTATATA CGCAAGTGAA ATCTCCTCCG                              40
```

(2) INFORMATION FOR SEQ ID NO: 10:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
CGATGCATCC AGGTAATGTA TTCTGTCAAT GCAGTTTGTA G                            41
```

(2) INFORMATION FOR SEQ ID NO: 11:

(i) SEQUENCE CHARACTERISTICS:
        (A) LENGTH: 410 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 11:

```
AGAACACGCG GACCTATATA CGCAAGTGAA ATCTCCTCCG TCTTGGAGAA GGGAGAGCGT        60

TTGCCCCAGC TACCATTGAT GTGTACATGA TCATGGTCAA ATGCTGGATG ATTGATGCAG        120

ACAGCCGTCC CAAGTTTCGT GAGCTGATTG CAGAGTTCTC CAAAATGGCT CGTGACCCTC        180

CCCGCTATCT TGTTATACAG GGAGATGAAA GGATGCACTT GCCTAGCCCT ACAGATTCCA        240

AGTTTTATCG CACCCTGATG GAGGAGGAGG ACATGGAAGA CATTGTGGAT GCAGATGAGT        300

ATCTTGTCCC ACACCAGGGC TTTTTCAACA TGCCCTCTAC ATCTCGGACT CCTCTTCTGA        360

GTTCATTGAG CGCTACTAGC AACAATTCTG CTACAAACTG CATTGACAGA                   410
```

(2) INFORMATION FOR SEQ ID NO: 12:

(i) SEQUENCE CHARACTERISTICS:
        (A) LENGTH: 388 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 12:

```
TGATTAACAA AATTATCATT TTTAAGAAAA AATGTATAAT TAATATTCTA TAATCTTCTC        60

TTGTTATCAA AAATTTTAAG GAGAAAGTCG ATGCATCCAG GTAATGTATT AAATTACGAC        120

TATACGGTTG CAAGATATTT TATGTTTGCG ACCATATTGT TTGGCATTGT TGGTATGGCT       180
```

```
ATAGGAACTC TTATAGCTTT TCAAATGGCA TATCCTAATT TAAATTATTT ACCAGGACAA      240

TATGCCACTT TTTCAAGACT TAGACCACTT CATACTTCAG GTGTGATTTT TGGTTTTATG      300

CTTTCAGGGA TTTGGGCAAC GGTATTATAT AGGTCCGCGT GTTCTTAAAG TGAGTATGGC      360

TGAGTCAAGA TTTTTAATGG CTGTTGGT                                        388
```

(2) INFORMATION FOR SEQ ID NO: 13:

(i) SEQUENCE CHARACTERISTICS:
        (A) LENGTH: 58 amino acids
        (B) TYPE: amino acid
        (D) TOPOLOGY: linear (ii) MOLECULE TYPE: protein (xi) SEQUENCE DESCRIPTION: SEQ ID NO: 13:

```
Tyr Asp Tyr Thr Val Ala Arg Tyr Phe Met Phe Ala Thr Ile Leu Phe
 1               5                  10                  15

Gly Ile Val Gly Met Ala Ile Gly Thr Leu Ile Ala Phe Gln Met Ala
            20                  25                  30

Tyr Pro Asn Leu Asn Tyr Leu Pro Gly Gln Tyr Ala Thr Phe Ser Arg
        35                  40                  45

Leu Arg Pro Leu His Thr Ser Gly Val Ile
    50                  55
```

(2) INFORMATION FOR SEQ ID NO: 14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 14:

```
Gln Asn Tyr His Phe
 1               5
```

(2) INFORMATION FOR SEQ ID NO: 15:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 15:

```
Glu Lys Met Tyr Asn
 1               5
```

(2) INFORMATION FOR SEQ ID NO: 16:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 16:

```
Leu Thr Lys Leu Ser Phe Leu Arg Lys Asn Val
 1               5                  10
```

(2) INFORMATION FOR SEQ ID NO: 17:

(i) SEQUENCE CHARACTERISTICS:
        (A) LENGTH: 102 amino acids
        (B) TYPE: amino acid
        (D) TOPOLOGY: linear (ii) MOLECULE TYPE: peptide (xi) SEQUENCE DESCRIPTION: SEQ ID NO: 17:

```
Leu Ile Phe Tyr Asn Leu Leu Leu Ser Lys Ile Leu Arg Arg Lys
 1               5                  10                  15

Ser Met His Pro Gly Asn Val Leu Asn Tyr Asp Tyr Thr Val Ala Arg
            20                  25                  30

Tyr Phe Met Phe Ala Thr Ile Leu Phe Gly Ile Val Gly Met Ala Ile
            35                  40                  45

Gly Thr Leu Ile Ala Phe Gln Met Ala Tyr Pro Asn Leu Asn Tyr Leu
            50                  55                  60

Pro Gly Gln Tyr Ala Thr Phe Ser Arg Leu Arg Pro Leu His Thr Ser
 65                  70                  75                  80

Gly Val Ile Phe Gly Phe Met Leu Ser Gly Ile Trp Ala Thr Val Leu
                85                  90                  95

Tyr Arg Ser Ala Cys Ser
            100
```

(2) INFORMATION FOR SEQ ID NO: 18:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 18:

```
Ser Glu Tyr Gly
 1
```

(2) INFORMATION FOR SEQ ID NO: 19:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 19:

```
Val Lys Ile Phe Asn Gly Cys Trp
 1               5
```

We claim:

1. A method of distinguishing between Campylobacter species, comprising:
   (a) identifying a selected Campylobacter DNA sequence, said sequence comprising one or more restriction endonuclease sites specifically associated with different Campylobacter species; and
   (b) testing for the presence within said selected sequence of one or more of said restriction endonuclease sites, thereby distinguishing between Campylobacter species *C. jejuni, C. coli, C. upsaliensis* and *C. lari,* wherein said DNA sequence comprises at least 72 nucleotides from SEQ ID NO: 1.

2. The method of claim 1, wherein a hybridization probe is used to distinguish between said Campylobacter species.

3. The method of claim 2, wherein said hybridization probe spans a restriction endonuclease site.

4. The method of claim 1, further comprising amplifying said selected Campylobacter sequence.

5. A method of distinguishing between Campylobacter species, comprising contacting a selected Campylobacter DNA sequence with a nucleic acid probe, wherein said selected Campylobacter DNA sequence comprises at least 72 nucleotides from SEQ ID NO:1 and contains one or more restriction endonuclease sites specifically associated with different Campylobacter species, and wherein said nucleic acid probe hybridizes with said selected Campylobacter DNA sequence.

6. The method of claim 5, wherein said nucleic, acid probe spans a restriction endonuclease site contained within said selected Campylobacter DNA sequence.

7. The method of claim 5, wherein said method distinguishes between Campylobacter species *C. jejuni, C. coli, C. upsaliensis* and *C. lari*.

8. The method of claim 5, wherein said selected Campylobacter sequence comprises nucleotides 124–196 of SEQ ID NO:1.

9. A nucleic acid probe for use in distinguishing between Campylobacter species, wherein said nucleic acid probe hybridizes to a restriction endonuclease site located within nucleotides 124–196 SEQ ID NO:1.

10. The method of claim 1, wherein *Campylobacter jejuni* is characterized by the presence of sites for endonucleases Alu I, Dde I and Dra I, *C. coli* is characterized by the absence of a site for endonuclease Dra I, *C. upsaliensis* is characterized by the absence of sites for endonucleases Alu I and Dra I, and *C. lari* is characterized by the presence of a site for endonuclease Alu I only.

11. The method of claim 7, wherein *Campylobacter jejuni* is characterized by the presence of sites for endonucleases Alu I, Dde I and Dra I, *C. coli* is characterized by the absence of a site for endonuclease Dra I, *C. upsaliensis* is characterized by the absence of sites for endonucleases Alu I and Dra I, and *C. lari* is characterized by the presence of a site for endonuclease Alu I only.

* * * * *